United States Patent
Brisebois et al.

(10) Patent No.: US 6,312,416 B1
(45) Date of Patent: Nov. 6, 2001

(54) THIN SANITARY NAPKIN CAPABLE OF CONTROLLED DEFORMATION WHEN IN USE

(75) Inventors: Henri Brisebois, Lachenaie; Louis Canuel, Repentigny; Christiane Lariviere, Montreal; Zulfikar Murji, Verdun, all of (CA)

(73) Assignee: Johnson & Johnson, Inc., Montreal (CA)

( * ) Notice: Subject to any disclaimer, the term of this patent is extended or adjusted under 35 U.S.C. 154(b) by 0 days.

(21) Appl. No.: 09/375,343

(22) Filed: Aug. 16, 1999

(51) Int. Cl.[7] .............................. A61F 13/15; A61F 13/20
(52) U.S. Cl. .................. 604/385.01; 604/378; 604/380; 604/358
(58) Field of Search ...................... 604/367, 369, 604/374, 378, 385.04, 385.01, 380

(56) References Cited

U.S. PATENT DOCUMENTS

| | | | |
|---|---|---|---|
| 5,171,302 | * 12/1992 | Buell | 604/385.1 |
| 5,197,959 | * 3/1993 | Buell | 604/385.1 |
| 5,505,719 | * 4/1996 | Cohen et al. | 604/372 |
| 5,578,025 | * 11/1996 | May | 604/385.1 |
| 5,891,121 | * 4/1999 | Redwine et al. | 604/387 |

* cited by examiner

*Primary Examiner*—John G. Weiss
*Assistant Examiner*—Michele Kidwell
(74) *Attorney, Agent, or Firm*—James P. Barr

(57) ABSTRACT

The present invention provides a sanitary napkin that is thin (less than 5 mm in thickness), highly absorbent and has a lateral flexibility allowing for controlled deformation when in use, namely the assumption of a "W" pattern (good for absorption performance) or a "M" pattern (which enhances comfort). This controlled deformation provides a good comfort potential and simultaneously reduces the likelihood of bunching due to compression forces exerted laterally against the napkin by the thighs of the wearer. In a specific example, the sanitary napkin is characterized by a lateral stiffness of not less than about 400 g and comprises a cover layer, a barrier layer and an second absorbent layer having at least one preferential bending zone which allows the napkin to adopt a certain three-dimensional deformation profile in response to lateral compression.

19 Claims, 6 Drawing Sheets

THIN SANITARY NAPKIN CAPABLE OF CONTROLLED DEFORMATION WHEN IN USE

FIELD OF THE INVENTION

The present invention relates generally to the art of fluid absorption and more particularly to a disposable sanitary napkin that is thin, highly absorbent and is capable of controlled deformation when in use.

BACKGROUND OF THE INVENTION

One element that contributes to the performance of a sanitary napkin is the way the napkin withstands deformation when in use. It has been observed that the thighs of an individual exert lateral forces on a sanitary napkin when the article is positioned for use on the undergarment. This results in bunching of the sanitary napkin, affecting the efficiency of the article's ability to collect bodily fluids since there is a concomitant reduction in the article's surface area. This observation is especially true for thin sanitary napkins that are highly flexible.

One approach to minimising this problem is to make the sanitary napkin stiffer in order that it may better withstand the effects of lateral compression. This approach may, however, have an adverse effect on the comfort potential of the sanitary napkin because the added stiffness affects the movement of the napkin in all directions, making it more difficult for the napkin to conform to the natural shape of the wearer's body.

Against this background, it can be seen that there exists a need to provide a sanitary napkin that is comfortable and yet reduces the likelihood of bunching when in use, leading to an overall increase in its efficiency for collecting bodily fluids.

SUMMARY OF THE INVENTION

It has been discovered that when a sanitary napkin is provided with at least one preferential bending zone in its absorbent system, the effect is to promote the folding of the absorbent system along this preferential zone and to promote a certain three-dimensional deformation profile in the napkin in response to lateral compression exerted by the thighs of the wearer. The sanitary napkin has a flexure resistance that is not less than about 400 g. This feature provides a sanitary napkin that is sufficiently stiff, so as to be stable enough and thus allow the sanitary napkin to fold in a predictable manner and avoid the likelihood of bunching when subjected to lateral compression.

In one aspect of the invention, the absorbent system of the sanitary napkin includes two preferential bending zones extending longitudinally near the side edges of the napkin and a central preferential bending zone extending longitudinally in the central portion of the absorbent system. In use, the sanitary napkin assumes a three-dimensional deformation profile that resembles the letter "W", in response to the lateral forces exerted by the thighs of the wearer. In a specific example of implementation, the sanitary napkin includes of a plurality of preferential bending lines that extend obliquely relative to the longitudinal axis of the napkin and intersect each other. The preferential bending lines cross one another and form an array of crossing points. The crossing points are located along the longitudinal axis of the sanitary napkin and structurally weaken the sanitary napkin at that location allowing the sanitary napkin to fold preferentially along its longitudinal axis. The array of crossing points forms the central preferential bending zone.

The preferential bending zone under any one of the aspects of the invention presented above may be realised by means of any one of the following: perforations, slits, cuts and embossing, as well as any other processes known to a person skilled in the art that has the effect of locally weakening the material in which the preferential bending zone is to be created.

Other aspects and features of the present invention will become apparent in those ordinarily skilled in the art upon review of the following description of specific embodiments of the invention in conjunction with the accompanying drawings.

DETAILED DESCRIPTION

Figure 1:
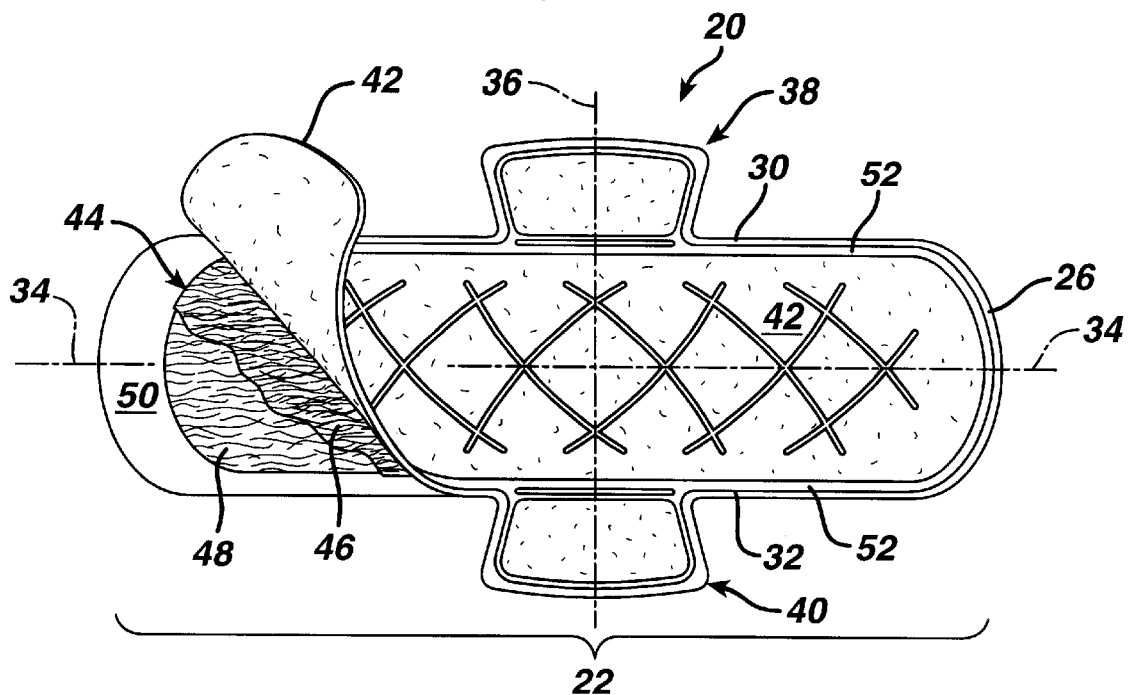
FIG. 1 is a top elevational view of a sanitary napkin in accordance with the present invention, the cover layer of the sanitary napkin being partly removed to show the absorbent system.
Figure 2:
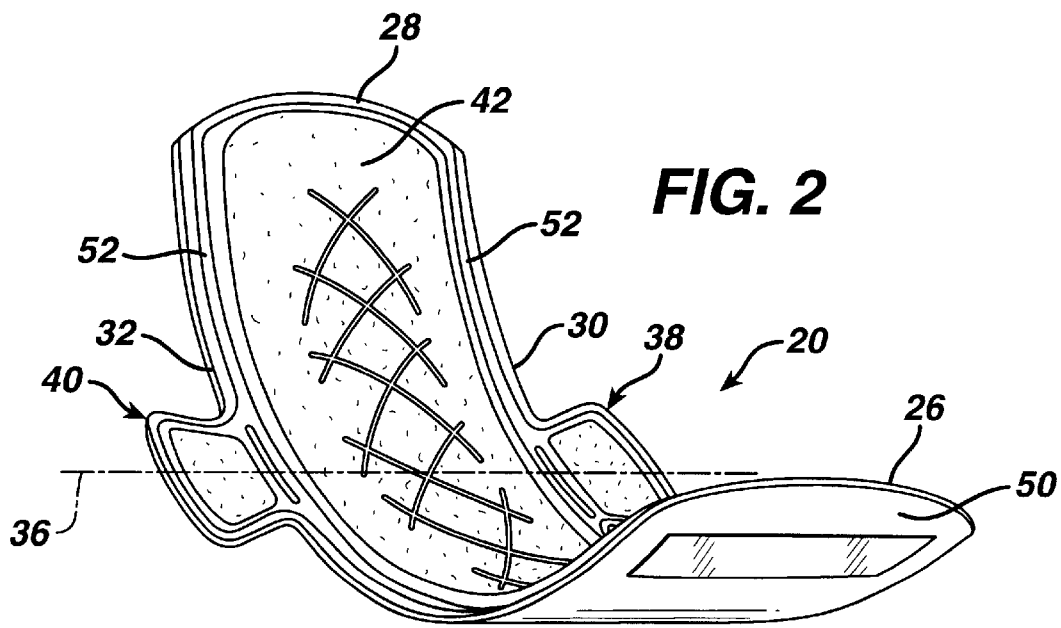
FIG. 2 is a perspective view of the sanitary napkin of FIG. 1, depicted in a position attained when the sanitary napkin is placed in the undergarment of a wearer.

Referring to FIGS. 1 and 2, there is shown an embodiment of the present invention, a feminine sanitary napkin 20.

The sanitary napkin 20 has a main body 22 with a first transverse side 26 defining a front portion thereof and a second transverse side 28 defining a rear portion thereof. Each of these sides is arcuate or of any other suitable shape. The main body also has two longitudinal sides, namely a longitudinal side 30 and a longitudinal side 32. The sanitary napkin 20 has a thickness not exceeding about 5 mm. Preferably, the thickness is less than 3.5 mm, more preferably less than 3 mm, and most preferably, it is of about 2.8 mm.

The sanitary napkin 20 has a longitudinal centerline 34 that is an imaginary line bisecting the sanitary napkin 20 in two identical halves.

In the embodiments shown in the drawings the sanitary napkin is provided with a pair of side flaps 38, 40. The flaps 38, 40 project laterally outward from each of the longitudinal sides 30, 32 and are adapted to be folded over a crotch portion of a wearers undergarment. The flaps 38, 40 are in the shape of an isosceles trapezoid with the top adjoining the longitudinal side and the base at the distal end.

The main body 22 also has an imaginary transverse centerline 36 perpendicular to the longitudinal centerline 34 and simultaneously bisecting the flaps 38, 40.

Figure 4:
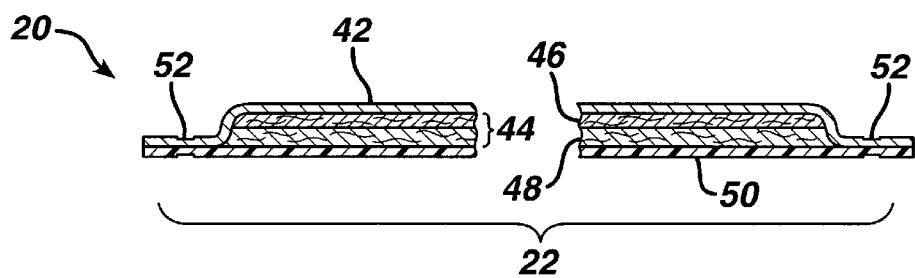
FIG. 4 is a cross-sectional view taken along the longitudinal centerline of the sanitary napkin shown in FIG. 3.

As depicted in FIG. 4, the main body 22 is of a laminate construction and preferably comprises a fluid-permeable cover layer 42, an absorbent system 44, and a fluid-impervious barrier layer 50. The absorbent system has preferably two components, namely a first absorbent layer 46 (commonly known as "transfer layer") and a second absorbent layer 48 (commonly known as "absorbent core"). Alternatively, a single layer, namely the second absorbent layer 48, can form the absorbent system 44. Each of these layers is described in hereinbelow.

Main Body—Cover Layer

The cover layer 42 may be a relatively low density, bulky, high-loft non-woven web material. The cover layer 42 may be composed of only one type of fiber, such as polyester or polypropylene or it may be composed of bi-component or conjugate fibers having a low melting point component and a high melting point component. The fibers may be selected from a variety of natural and synthetic materials such as nylon, polyester, rayon (in combination with other fibers), cotton, acrylic fiber and the like and combinations thereof. An example is the non-woven cover layer of sanitary napkins sold by Johnson & Johnson Inc. of Montreal, Canada under the trademark Stayfree Ultra-Thin Cottony Dry Cover.

Bi-component fibers may be made up of a polyester core and a polyethylene sheath. The use of appropriate bi-component materials results in a fusible non-woven fabric. Examples of such fusible fabrics are described in U.S. Pat. No. 4,555,446 issued Nov. 50, 1985 to Mays. Using a fusible fabric increases the ease with which the cover layer may be mounted to the adjacent first absorbent layer and/or to the barrier layer.

The cover layer 42 preferably has a relatively high degree of wettability, although the individual fibers comprising the cover may not be particularly hydrophilic. The cover material should also contain a great number of relatively large pores. This is because the cover layer 42 is intended to take-up body fluid rapidly and transport it away from the body and the point of deposition. Advantageously, the fibers which make up the cover layer 42 should not lose their physical properties when they are wetted, in other words they should not collapse or lose their resiliency when subjected to water or body fluid. The cover layer 42 may be treated to allow fluid to pass through it readily. The cover layer 42 also functions to transfer the fluid quickly to the other layers of the absorbent system 44. Thus, the cover layer 42 is advantageously wettable, hydrophilic and porous. When composed of synthetic hydrophobic fibers such as polypropylene or bi-component fibers, the cover layer 42 may be treated with a surfactant to impart the desired degree of wettability.

Alternatively, the cover layer 42 can also be made of polymer film having large pores. Because of such high porosity, the film accomplishes the function of quickly transferring body fluid to the inner layers of the absorbent system. Apertured co-extruded films such as described in U.S. Pat. No. 4,690,679 and available on sanitary napkins sold by Johnson & Johnson Inc. of Montreal, Canada could be useful as cover layers in the present invention.

The cover layer 42 may be embossed to the remainder of the absorbent system 44 in order to aid in promoting fluid transport by fusing the cover to the next layer. Such fusion may be effected locally, at a plurality of sites or over the entire contact surface of cover layer 42 with absorbent system 44. Alternatively, the cover layer 42 may be attached to the absorbent system 44 by other means such as by adhesive.

Main Body—Absorbent System—First Absorbent Layer

Adjacent to the cover layer 42 on its inner side and bonded to the cover layer 42 is a first absorbent layer 46 that forms part of the absorbent system 44. The first absorbent layer 46 provides the means of receiving body fluid from the cover layer 42 and holding it until an underlying second absorbent layer has an opportunity to absorb the fluid.

The first absorbent layer 46 is, preferably, more dense than and has a larger proportion of smaller pores than the cover layer 42. These attributes allow the first absorbent layer 46 to contain body fluid and hold it away from the outer side of the cover layer 42, thereby preventing the fluid from re-wetting the cover layer 42 and its surface. However, the first absorbent layer 46 is, preferably, not so dense as to prevent the passage of the fluid through the layer 46 into the underlying second absorbent layer 48. These types of absorbent layers are commonly known as fluid transfer layers or acquisition layers.

The first absorbent layer 46 may be composed of fibrous materials, such as wood pulp, polyester, rayon, flexible foam, or the like, or combinations thereof. The first absorbent layer 46 may also comprise thermoplastic fibers for the purpose of stabilizing the layer and maintaining its structural integrity. The first absorbent layer 46 may be treated with surfactant on one or both sides in order to increase its wettability, although generally the first absorbent layer 46 is relatively hydrophilic and may not require treatment. The first absorbent layer 46 is preferably bonded on both sides to the adjacent layers, i.e. the cover layer 42 and an underlying second absorbent layer 48. An example of a suitable first absorbent layer is a through air bonded pulp sold by BUCK-EYE of Memphis Tennessee under the designation VIZORB 3008.

Main Body—Absorbent System—Second Absorbent Layer

Immediately adjacent to and bonded to the first absorbent layer 46 is the second absorbent layer 48.

In one embodiment, the first absorbent layer 46 has a central width that is at least about the same as the central Width of the second absorbent layer 48. In a specific embodiment, this central width is greater than about 64 mm. In another embodiment, the first absorbent layer 46 has a central width that exceeds the central width of the second absorbent layer 48. The term "central width" refers to a specific area of a layer, such as an absorbent layer determinable as follows. A reference point on the sample layer that is disposed beneath the center of the vaginal orifice, when worn, is located. A plane parallel to the transverse centerline 36 and 3.75 centimeters forward from the reference point in the direction of the wearer's mons pubis is located. Another plane parallel to the lateral centerline 36 and 5.0 centimeters rearward from the reference point in the direction of the wearer's buttocks is also located. The greatest flat-out, uncompressed, unmanipulated, lateral width of the sample layer between the two planes is the absorbent width of the sample layer.

The central width of the absorbent system, when the absorbent system includes a plurality of absorbent layers is the central width of the layer of the absorbent system that has the largest central width. In a specific example, the central width of the absorbent system exceeds 64 mm.

In one embodiment, the second absorbent layer 48 is a blend or mixture of cellulosic fibers and superabsorbent disposed in and amongst fibers of that pulp.

In a specific example, the second absorbent layer 48 is a material containing from about 40 weight percent to about 95 weight percent cellulosic fibers; and from about 5 weight percent to about 60 weight percent SAP (superabsorbent polymers). The material has a water content of less than about 10 weight percent. As used herein, the phrase "weight percent" means weight of substance per weight of final material. By way of example, 10 weight percent SAP means 10 g/m2 SAP per 100 g/m2 basis weight of the material.

Cellulosic fibers that can be used in the second absorbent layer 48 are well known in the art and include wood pulp, cotton, flax and peat moss. Wood pulp is preferred. Pulps can be obtained from mechanical or chemi-mechanical, sulfite, kraft, pulping reject materials, organic solvent pulps, etc. Both softwood and hardwood species are useful. Softwood pulps are preferred. It is not necessary to treat cellulosic fibers with chemical debonding agents, cross-linking agents and the like for use in the present material.

The second absorbent layer 48 can contain any superabsorbent polymer (SAP), which SAPs are well known in the art. For the purposes of the present invention, the term "superabsorbent polymer" (or "SAP") refers to materials which are capable of absorbing and retaining at least about 10 times their weight in body fluids under a 0.5 psi pressure. The superabsorbent polymer particles of the invention may be inorganic or organic crosslinked hydrophilic polymers, such as polyvinyl alcohols, polyethylene oxides, crosslinked starches, guar gum, xanthan gum, and the like. The particles may be in the form of a powder, grains, granules, or fibers. Preferred superabsorbent polymer particles for use in the present invention are crosslinked polyacrylates, such as the product offered by Sumitomo Seika Chemicals Co., Ltd. Of Osaka, Japan, under the designation of SA60N Type II*, and the product offered by Chemdal International, Inc. of Palatine, Ill., under the designation of 2100A*.

In a specific example the second absorbent layer 48 is a material containing from about 50 to about 95 weight percent cellulosic fibers and, more specifically from about 60 to about 80 weight percent cellulosic fibers. Such a material may contain from about 5 to about 60 weight percent SAP, preferably from about 20 to about 55 weight percent SAP, even more preferably from about 30 to about 45 weight percent SAP, and most preferably about 40 weight percent SAP.

Figure 5:
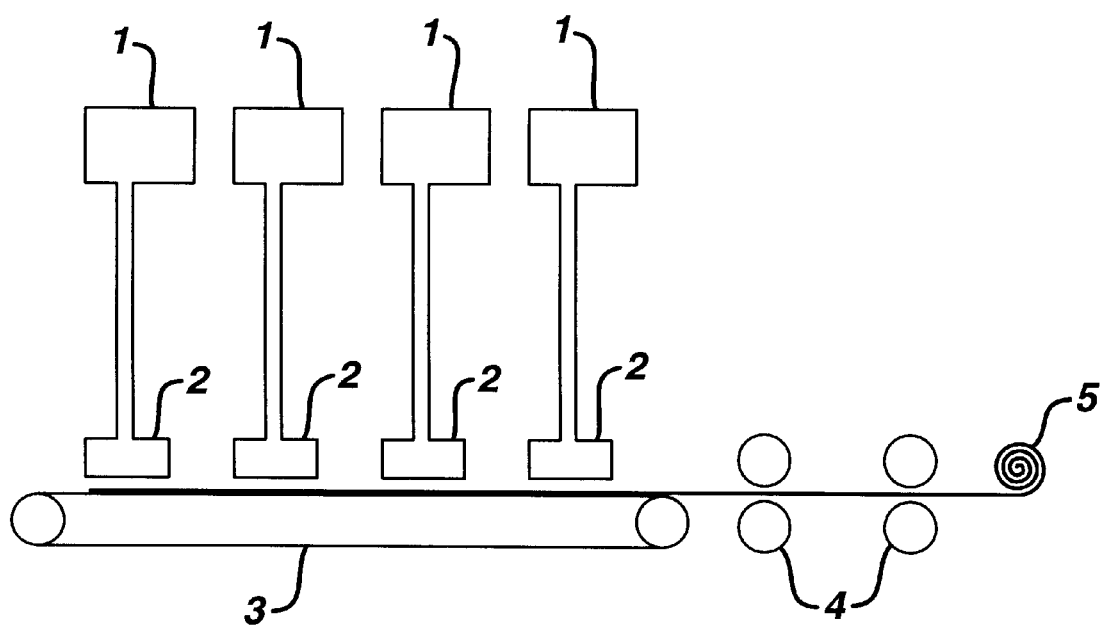
FIG. 5 is a schematic illustration of means for air-laying absorbent material for making an example of an absorbent layer of the absorbent system of the sanitary napkin according to the invention, using four air-laying heads followed by means for compacting the air-laid material.

The second absorbent layer 48 can be manufactured by using air-laying means well known in the art (See FIG. 5). In accordance with FIG. 5, cellulosic fibers (e.g., pulp) are processed using a hammer mill to individualize the fibers. The individualized fibers are blended with SAP granules in a blending system 1 and pneumatically conveyed into a series of forming heads 2. The blending and distribution of fibers and SAP granules can be controlled separately for each forming head. Controlled air circulation and winged agitators in each chamber produce uniform mixture and distribution of pulp and SAP. The SAP can be thoroughly and homogeneously blended throughout the material or contained only in specific strata by distributing it to selected forming heads. Fibers (and SAP) from each forming chamber are deposited by vacuum onto a forming wire 3 thus forming a layered absorbent web. The web is subsequently compressed using calenders 4 to achieve desirable density. The densified web is wound into a roll 5 using conventional winding equipment. The forming wire 3 can be covered with tissue paper to reduce the loss of material. The tissue paper layer can be removed prior to calendering or incorporated into the formed material. In a possible variant, the first absorbent layer 46 can be formed integrally with the second absorbent layer 48 to provide a unitized absorbent system 44. This can be achieved by providing the apparatus depicted in FIG. 5 with an additional forming head (not shown in the drawings) to deposit on the second absorbent layer 48, by air laying and prior to calendering, a layer of material to form the first absorbent layer 46.

The second absorbent layer 48 of the present invention is of high density and in a specific example has a density of greater than about 0.25 g/cc. Specifically, the second absorbent layer 48 may have a density in the range of from about 0.30 g/cc to about 0.50 g/cc. More specifically, the density is from about 0.30 g/cc to about 0.45 g/cc and, even more specifically from about 0.35 g/cc to about 0.40 g/cc.

Air-laid absorbents are typically produced with a low density. To achieve higher density levels, such as the examples of the second absorbent layer 48 given above, the air-laid material is compacted using calenders as shown in FIG. 5. Compaction is accomplished using means well known in the art. Typically such compaction is carried out at a temperature of about 100 degrees C. and a load of about 130 Newtons per millimeter. The upper compaction roll is typically made of steel while the lower compaction roll is a flexroll having a hardness of about 85 SH D. It is preferred that both the upper and lower compaction rolls be smooth, although the upper roll can be engraved.

In one embodiment the second absorbent layer 48 has a ratio of Gurley stiffness, measured in milligrams (mg) to density, measured in grams per cubic centimeter (g/cc), of less than about 3700. In a specific example, that ratio of Gurley stiffness to density is less than about 3200 and, more specifically, less than about 3000.

Gurley stiffness is one of many indices of softness. Gurley stiffness measures the bendability or flexibility of absorbent materials. The lower the Gurley stiffness value, the more flexible the material. The Gurley stiffness values are measured using a Gurley Stiffness Tester (Model No. 4171E), manufactured by Gurley Precision Instruments of Troy, N.Y. The instrument measures the externally applied moment required to produce a given deflection of a test strip of specific dimensions fixed at one end and having a concentrated load applied to the other end. The results are obtained in "Gurley Stiffness" values in units of milligrams.

The second absorbent layer 48 is strong in light of its softness. Pad integrity is a well-known measurement of absorbent material strength. In a specific embodiment the second absorbent layer 48 demonstrates strength (high pad integrity) over a wide range of densities. In a specific example the second absorbent layer 48 has a pad integrity, measured in Newtons (N), to density (g/cc) ratio of greater than about 25.0. In a more specific example, that ratio is greater than about 30.0 and, could even be greater than about 35.0. The pad integrity is a test performed on an Instron Universal Testing Machine. Essentially, the test measures the load required to pierce through the test sample, as described in the PFI Method of 1981. A test sample having dimensions of 50 mm by 50 mm is damped on the Instron with a suitable fastening device. A 20 mm diameter piston traveling at the rate of 50 mm/min punctures the stationary sample. The force required to puncture the sample is measured in Newtons (N).

The second absorbent layer 48 can be prepared over a wide range of basis weights. The second absorbent layer 48 can have a basis weight in the range of from about 100 g/m2 to about 700 g/m2. In a specific example, the basis weight ranges from about 150 g/m2 to about 350 g/m2. Preferably the basis weight ranges from about 200 g/m2 to about 300 g/m2 and, more preferably, to about 250 g/m2.

The second absorbent layer 48 can be formed as three or four lamina or strata. Those strata include a bottom layer, one or two middle layers and a top layer. Specific examples of three and four layer material are set forth below. The SAP can be included in any or all of the layers. The concentration (weight percent) of SAP in each layer can vary as can the nature of the particular SAP.

An interesting characteristic of the second absorbent layer 48 is its ability to retain SAP when subjected to mechanical stress. The second absorbent layer 48 retained over 85 percent by weight of its SAP content when subjected to 10 minutes of rigorous shaking. Specifically, a material of this invention retains over 90 percent, more specifically over 95 percent and, even more specifically over 99 percent of its SAP under these mechanical stresses. The percent of SAP retained was determined by shaking the material in a Ro-Tap Sieve Shaker manufactured by W. S. Tyler Co., Cleveland Ohio. More specifically the sample is placed in a 28-mesh (Tyler series) sieve. Additional sieves of 35-mesh and 150-mesh were attached to the first sieve forming a column of increasingly fine sieves. The column of sieves was capped on either end to prevent the loss of fiber and/or SAP. The sieve column was placed in the shaker and agitated for 10 minutes. The amount of SAP granules shaken loose from the sample, "free SAP", was determined by combining the residue contained in each of the sieves and separating the cellulosic fiber from the SAP.

Even where prepared as from multiple layers, the final thickness of the formed second absorbent layer 48 is low. The thickness can vary from about 0.5 mm to about 2.5 mm. In a specific example, the thickness is from about 1.0 mm to about 2.0 mm and, even more specifically from about 1.25 mm to about 1.75 mm.

Figure 6A:
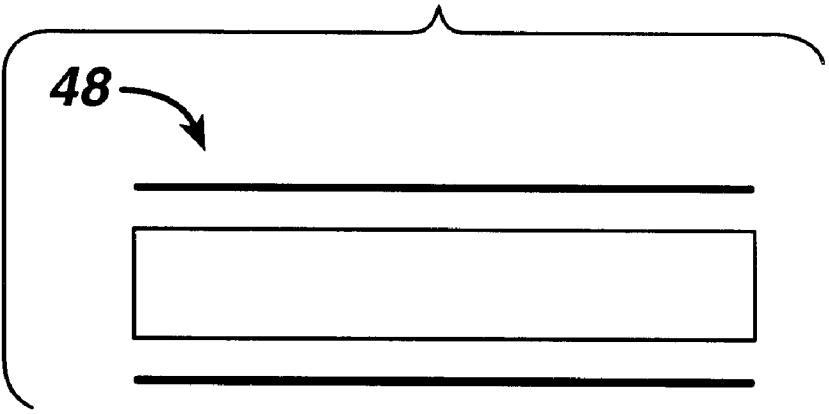
FIGS. 6(*a*) and 6(*b*) show three and four stratum embodiments, respectively, of an absorbent layer that can be used in the construction of the absorbent system of the sanitary napkin in accordance with the invention.
Figure 6B:
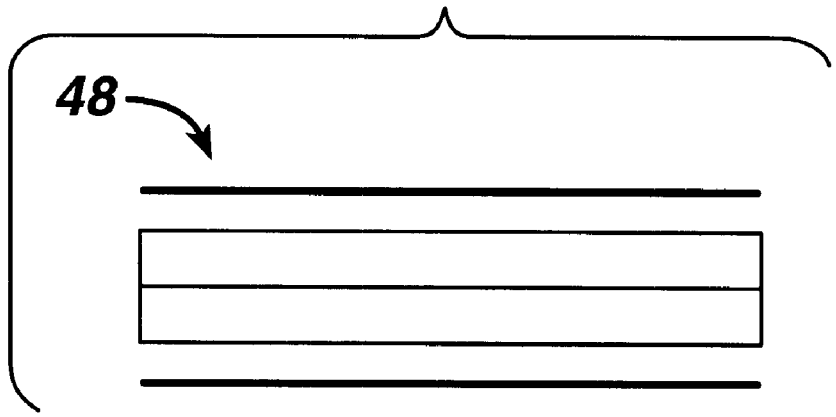

One embodiment of the second absorbent layer 48 particularly well suited for use in the sanitary napkin 20 is depicted in FIG. 6. Such second absorbent layer 48 has a basis weight of from about 200 g/m2 to about 350 g/m2 and a density between about 0.3 g/cc and 0.5 g/cc. In a specific example, the density is from about 0.3 g/cc to about 0.45 g/cc and, more specifically about 0.4 g/cc.

The second absorbent layer 48 depicted in FIG. 6(*a*) is air-laid as three strata: a bottom layer of pulp (without superabsorbent) with a basis weight of about 25 g/m2; a middle layer with a basis weight of about 150 g/m2 and which contains from about 10 to about 30 g/m2 superabsorbent and from about 120 g/m2 to about 140 g m2 pulp; and a top layer of pulp (without superabsorbent) with a basis weight of about 25 g/m2. Relative to the total basis weight of the second absorbent layer 48, the level of superabsorbent ranges from about 5 to about 15 weight percent (g/m2 of superabsorbent per g/m2 material). In a specific example, the level of superabsorbent is from about 7.5 weight percent to about 12.5 weight percent of the material. More specifically, the material contains about 10 weight percent of superabsorbent. Thus, the middle layer of the material could contain from about 15 g/m2 to about 25 g/m2 superabsorbent and from about 125 g/m2 to about 135 g/m2 pulp and, more specifically about 20 g/m2 superabsorbent and about 130 g/m2 pulp. The middle layer containing pulp and superabsorbent can be laid down as a homogeneous blend or as a heterogeneous blend wherein the level of superabsorbent varies with proximity to the bottom layer.

In another embodiment depicted in FIG. 6(*b*), the second absorbent layer 48 is air-laid as four strata. In this embodiment, the middle layer referred to above is replaced with two middle layers: a first middle layer adjacent the top layer and a second middle layer adjacent the bottom layer. Each of the first and second middle layers independently comprises from about 10 to about 30 g/m2 superabsorbent and from about 40 g/m2 to about 65 g/m2 pulp. When it is desired to keep absorbed fluid away from the cover layer 42 the amount of superabsorbent in the first and second middle layers is adjusted such that there is a higher level of superabsorbent in the second middle layer. The superabsorbent in the first and second middle layers can be the same or a different superabsorbent.

In one embodiment, the cellulosic fiber for use in the second absorbent layer 48 is wood pulp. There are certain characteristics of wood pulp that make it particularly suitable for use. Cellulose in most wood pulps has a crystalline form known as Cellulose I which can be converted to a form known as Cellulose II. In the second absorbent layer 48, wood pulp with a substantial portion of the cellulose as Cellulose II could be used. Similarly, pulps having an increased fiber curl value are advantageous. Finally, pulps having reduced levels of hemicellulose are preferred. Means for treating pulps so as to optimize these characteristics are well known in the art. By way of example, treating wood pulp with liquid ammonia is known to convert cellulose to the Cellulose II structure and to increase the fiber curl value. Flash drying is known to increase the fiber curl value of pulp. Cold caustic treatment of pulp decreases hemicellulose content, increases fiber curl and converts cellulose to the Cellulose II form. Thus it could be advantageous that the cellulosic fibers used to produce the material of this invention contain at least a portion of cold caustic treated pulp.

A description of the cold caustic extraction process can be found in U.S. patent application Ser. No. 08/370,571, filed on Jan. 18, 1995, pending which application is a continuation-in-part application of U.S. patent application Ser. No. 08/184,377, now abandoned filed on Jan. 21, 1994. The disclosures of both of these applications are incorporated in their entirety herein by reference.

Briefly, a caustic treatment is typically carried out at a temperature less than about 60 degree C., but preferably at a temperature less than 50 degree C., and more preferably at a temperature between about 10 degree C. to 40 degree C. A preferred alkali metal salt solution is a sodium hydroxide solution newly made up or as a solution by-product in a pulp or paper mill operation, e.g., hemicaustic white liquor, oxidized white liquor and the like. Other alkali metal salts such as ammonium hydroxide and potassium hydroxide and the like can be employed. However, from a cost standpoint, the preferable salt is sodium hydroxide. The concentration of alkali metal salts is typically in a range from about 2 to about 25 weight percent of the solution, and preferably from about 6 to about 18 weight percent. Pulps for high rate, fast absorbing applications are preferably treated with alkali metal salt concentrations from about 10 to about 18 weight percent.

For further details on the structure and the method of construction of the second absorbent layer 48 the reader is invited to refer to the U.S. Pat. No. 5,866,242 granted on Feb. 2, 1999 to Tan et al. The contents of this document are hereby incorporated by reference.

Main Body—Barrier Layer

Underlying the absorbent system 44 is a barrier layer 50 comprising liquid-impervious film material so as to prevent liquid that is entrapped in the absorbent system 44 from egressing the sanitary napkin and staining the wearers undergarment. The barrier layer 50 is made preferably of polymeric film.

The cover layer 42 and the barrier layer 50 are joined along their marginal portions so as to form an enclosure or flange seal that maintains the absorbent system 44 captive. The joint may be made by means of adhesives, heat-bonding, ultrasonic bonding, radio frequency sealing, mechanical crimping, and the like and combinations thereof. The peripheral seal line is shown in FIG. 1 by the reference numeral 52.

Flaps

The flaps 38 and 40 are preferably made as integral extensions of the cover layer 42 and the barrier layer 50. These integral extensions are joined to one another along their marginal seal portions by adhesives, heat-bonding, ultrasonic bonding, radio frequency sealing, mechanical crimping, and the like and combinations thereof. Most preferably, such joining is made at the same time the cover layer 42 and the barrier layer 50 are bonded to one another to enclose the absorbent system 44. Alternatively, the flaps may include absorbent material between the cover layer and the barrier layer extensions. Such absorbent material may be an extension of the first absorbent layer 46, the second absorbent layer 48 or both.

Adhesive System

Figure 3:
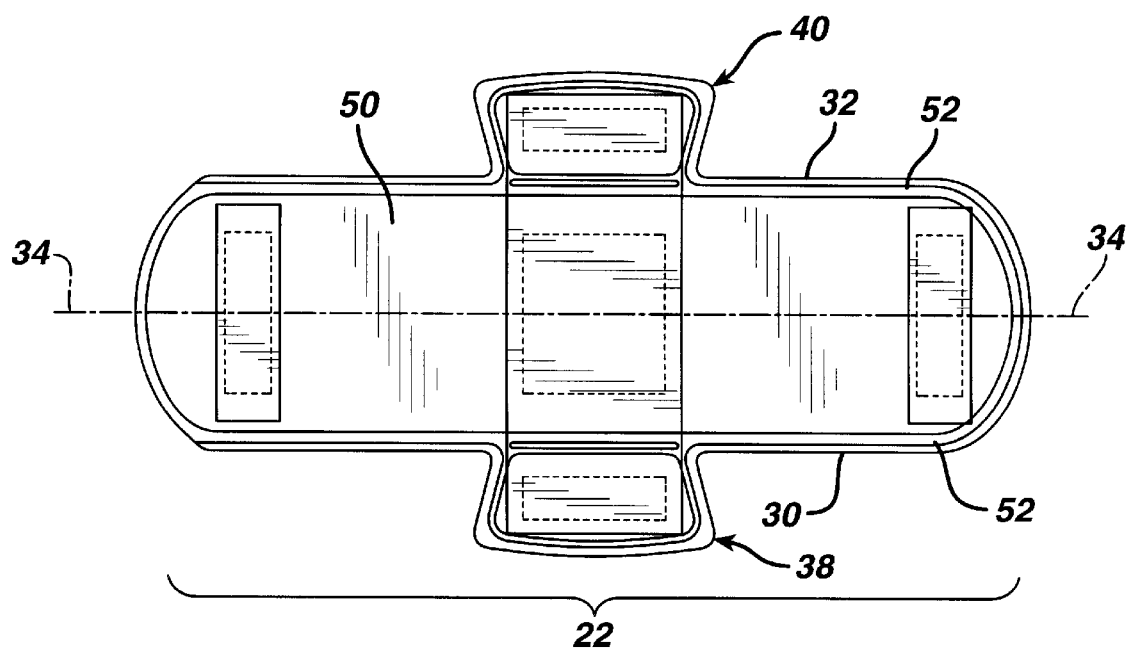
FIG. 3 is a bottom plan view of the sanitary napkin shown in FIG. 1.

Referring to FIGS. 2 and 3, in order to enhance the stability of the sanitary napkin, the garment facing surface of the barrier layer is provided with positioning adhesive material 58, typically hot-melt adhesive material capable of establishing a temporary bond with the undergarment material. A suitable material is the composition designated HL-1491 XZP commercially available from H. B. Fuller Canada, Toronto, Ontario, Canada. The positioning adhesive 58 may be applied to the garment-facing surface of the barrier layer 50 in various patterns, including complete adhesive coverage, parallel longitudinal lines, a line of adhesive following the perimeter of the structure, transverse lines of adhesive or the like.

Standard release paper 82 (shown only in FIG. 3) covers the positioning adhesive 58 before the napkin is used to prevent the unwanted adherence of the napkin to itself or foreign objects. The release paper is of conventional construction (e.g. silicone coated wet-laid Kraft wood pulp) and suitable papers are available from Tekkote Corporation (Leonia, N.J., U.S.A.), and bear the designation FRASER 30#/61629.

Figure 11:
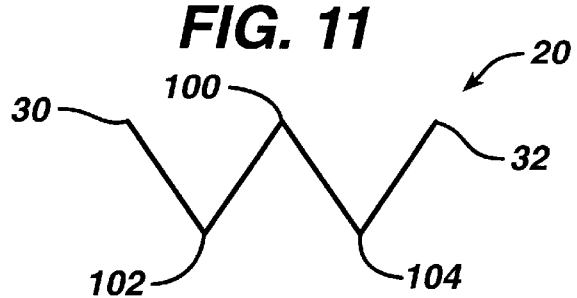
FIG. 11 is a cross-sectional view of the sanitary napkin shown in FIG. 1, depicting the napkin folded according to a "W" pattern.
Figure 12:
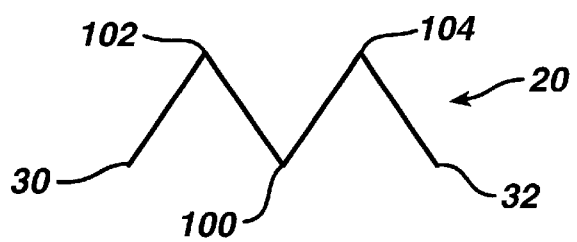
FIG. 12 is a cross-sectional view of the sanitary napkin shown in FIG. 1, depicting the napkin folded according to a "M" pattern.

The main body of the sanitary napkin is provided with at least one bending zone and preferably a pattern of bending zones to assist the sanitary napkin in folding according to a certain three-dimensional profile in use. In this specification, "three-dimensional deformation profile" means a deformation in the Z direction (vertical direction). FIGS. 11 and 12 illustrate examples of such three-dimensional profiles. FIG. 11 shows the sanitary napkin 20 of FIG. 1 in cross-section acquiring the "W" pattern where the central portion of the sanitary napkin 20 is raised to form a central upper apex while the zones of the sanitary napkin 20 between the central zone and the longitudinal sides 30, 32 are folded down to form two down apexes. This folding configuration is considered to reduce the likelihood of leakage by virtue of the central upper apex that is positioned close to the vaginal opening of the user, thus it is close to the source of the liquid discharge and as such can better acquire the liquid.

FIG. 12 illustrates the sanitary napkin 20 of FIG. 1 in cross-section acquiring the "M" pattern where the central portion of the sanitary napkin 20 is lowered to form a central down apex while the zones of the sanitary napkin 20 between the central zone and the longitudinal sides 30, 32 are folded up to form two upper apexes. This folding configuration is considered to enhance the comfort potential of the sanitary napkin 20 by locating the central portion of the sanitary napkin away from the body, thus reducing contact of the surface of the sanitary napkin with the body of the user. The centre of the "M" also forms a receptacle accommodating the labia majora of the user and capable of capturing a fluid discharge emanating therefrom.

The exemplary sanitary napkin construction depicted in FIG. 1, features a pattern of bending zones having three components, namely a central bending zone 100 and two linear longitudinally extending preferential bending zones 102 and 104. The longitudinally extending preferential bending zones 102 and 104 are located between the central bending zone 100 and the side edges 30, 32 of the sanitary napkin 20.

Figure 13:
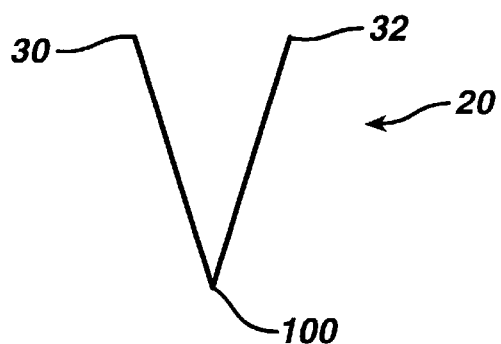
FIG. 13 is a cross-sectional view of the sanitary napkin shown in FIG. 1, depicting the napkin folded according to a "V" pattern.
Figure 14:
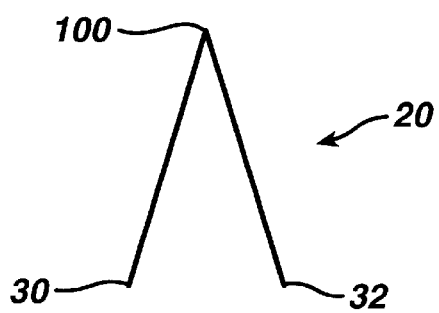
FIG. 14 is a cross-sectional view of the sanitary napkin shown in FIG. 1, depicting the napkin folded according to an inverted "V" pattern.

The sanitary napkin includes an array of oblique preferential bending lines intersecting each other to create a pattern extending over a major portion of the longitudinal dimension of the main body. The oblique preferential bending lines are arcuate and are created on the cover layer and absorbent system. Under this specific example of implementation, the preferential bending lines cross one another and form an array of crossing points. The crossing points are located substantially along the longitudinal axis of the sanitary napkin and structurally weaken the sanitary napkin at that location allowing the sanitary napkin to fold preferentially along a longitudinal axis to form an up apex of a V profile as shown in FIG. 13, or a down apex of an inverted V profile as shown in FIG. 14, when subjected to lateral compression. It is the array of crossing points that forms the preferential bending zone 100 substantially along the longitudinal center line of sanitary napkin 20.

Each preferential bending line of the array of bending lines extends generally along an angle of 45 degrees with respect to the longitudinal axis of the main body of the sanitary napkin. The pattern is designed such that each preferential bending line intersects at least two other preferential bending lines. Also, each preferential bending line extends from one longitudinal side area of the sanitary napkin to the opposite longitudinal side area, crossing the imaginary longitudinal axis of the sanitary napkin. A longitudinal side area is defined as a portion of the sanitary napkin that extends inwardly from a respective longitudinal side edge 30, 32, the side edge forming the outer boundary of the side area (the longitudinal side edge is considered part of the longitudinal side area). Each side area has a width that is about 25% of the maximal transverse dimension of the main body 22 (excluding the flaps).

In a preferred embodiment, the array of bending lines forms a first preferential bending zone substantially along the central longitudinal axis of sanitary napkin 20 and second and third preferential bending zones within the longitudinal side areas of the sanitary napkin 20. In this preferred embodiment, the preferential bending zones are formed by the intersections of the array of bending lines causing the cross-section of the sanitary napkin 20 to acquire an "M" profile where the first preferential bending zone substantially along the central axis of the sanitary napkin forms a down apex, and the second and third preferential bending zones within the longitudinal side areas form up apexes; or a "W" profile where the first preferential bending zone substantially along the central axis of the sanitary napkin forms an up apex, and the second and third preferential bending zones within the longitudinal side areas form down apexes.

Without intent of being bound by a specific theory, it is believed that the plurality of oblique preferential bending lines contribute to increase the flexure resistance to lateral compression of the sanitary napkin which has the effect of stabilising the sanitary napkin against bunching. At the same time, the oblique preferential bending lines form the central preferential bending zone at their crossing points.

In a specific example, the spacing between preferential bending lines is about 2 cm.

In a further embodiment of the sanitary napkin 20 of the invention, wherein the sanitary napkin has side flaps 38, 40, the second and third preferential bending zones are formed along the longitudinal side edges of the sanitary napkin at the junction of the side flaps with the side edge. In this embodiment, the first absorbent layer preferably has a width that is greater than the width of the second absorbent layer so that longitudinal side edges of the first absorbent layer extend beyond longitudinal side edges of the second absorbent layer. The second and third preferential bending zones may be formed by an array of preferential bending lines or by the junctions of the side flaps with the respective longitudinal side edges of the napkin or by the longitudinal side edges of the first absorbent layer. In cross-section the sanitary napkin of this embodiment may acquire an "M" profile or a "W" profile.

In an alternative embodiment, the array of preferential bending lines are created on the absorbent system only, such as on the first absorbent layer 46, the second absorbent layer 48 or both, so that the preferential bending lines are less visible on the sanitary napkin than when the preferential bending lines are made on the cover layer and absorbent system.

In another alternative embodiment, a single longitudinally extending continuous bending line extending along the longitudinal axis of the sanitary napkin can replace the array crossing points.

As discussed earlier, the pattern of bending zones on the sanitary napkin 20 can assist the sanitary napkin to acquire a three-dimensional deformation profile. The three-dimensional deformation profile includes either a "W" or an "M" profile, among other possible profiles. One profile can be privileged over the other type of deformation profile by controlling on which main surface (top surface or bottom surface) of the second absorbent layer the pattern of bending zones is distributed. The embodiment of the invention shown in FIG. 1 is designed to preferentially fold according to the "W" pattern. When the sanitary napkin 20 is subjected to lateral compression, it folds up at the longitudinal axis forming a central apex at that location and also folds down at the two longitudinally extending preferential bending zones 102 and 104 forming two down apexes.

Figure 7:
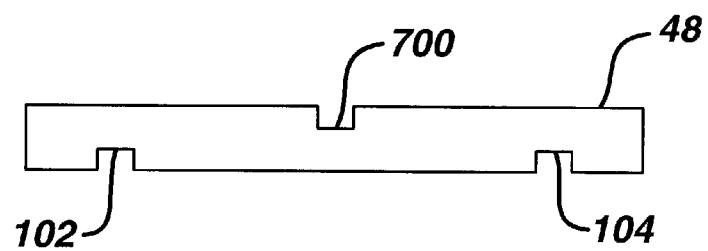
FIGS. 7 to 10 are cross-sectional views of an absorbent layer of the absorbent system of the sanitary napkin in accordance with the invention featuring different patterns of preferential bending zones allowing the sanitary napkin to fold in use according to a certain three-dimensional pattern.

FIG. 7 is a cross-sectional view of the second absorbent layer 48. The second absorbent layer 48 includes a pattern of bending zones comprising a central longitudinally extending bending zone 700 formed on the upper main surface of the second absorbent layer 48 and extending along the longitudinal axis of the second absorbent layer 48 that coincides with the longitudinal axis of the sanitary napkin 20. Preferably, the bending zone 700 extends the full length of the second absorbent layer 48. The longitudinally extending lateral bending zones 102 and 104 are formed on the lower main surface of the second absorbent layer 48.

In use, a sanitary napkin 20 with the second absorbent layer shown in FIG. 7, when subjected to lateral compression will more easily acquire the "W" pattern shown in FIG. 11.

Figure 8:
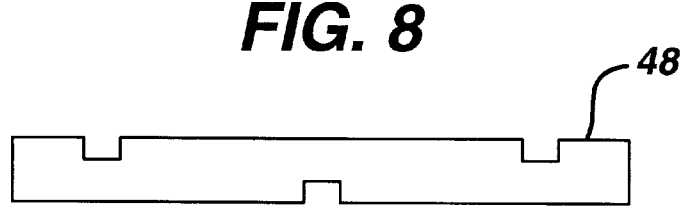

FIG. 8 is a variant of the second absorbent layer 48 shown in FIG. 7, where the position of the preferential bending zones has been reversed by comparison to the embodiment of FIG. 7. This provides a structure that more easily fold according to the "M" pattern shown in FIG. 12.

Figure 9:
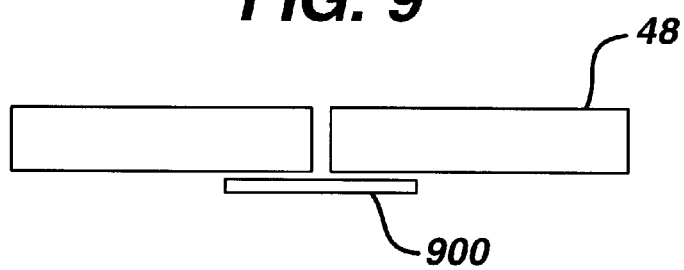

FIG. 9 is yet another variant where the preferential bending zone 700 is materialised by a slit that parts the second absorbent layer 48 in two separate halves. To control the deformation of the second absorbent layer, an optional abutment member 900 is placed under the slit such that the second absorbent layer 48 when subjected to lateral compression will fold up (inverted V shape) in the centre. The abutment member 900 can be a strip of synthetic foam material that extends under both halves of the second absorbent layer 48. This structure favours the formation of the "W" pattern in use. A variant is to make the slit shorter than the length of the second absorbent layer 48 such that the slit does not part the second absorbent layer 48 in two. Also, the slit can be replaced by a series of small perforations behaving as a preferential bending zone.

Figure 10:
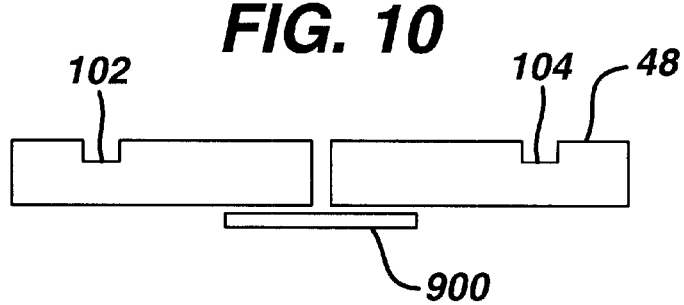

FIG. 10 shows yet another variant of the second absorbent layer 48 that is identical to the example depicted in FIG. 8 with the exception of the lateral longitudinally extending bending zones 102 and 104 formed on the upper main surface of the second absorbent layer 48. This structure also favours the formation of the "W" pattern in use.

Method of Manufacture

The above-described embodiment of the sanitary napkin 20 is fabricated in a conventional manner in accordance with conventional techniques. Specifically, a laminate structure, sometimes referred to in the art as a web, is created. This laminate structure comprises an expanse of the materials from which the napkin will be created. I.e. the laminate structure comprises the following layers of material in a top-to-bottom order: an expanse of cover layer material; an expanse of first absorbent layer material; an expanse of second absorbent layer material (manufactured as described above); and finally an expanse of barrier layer material. Some of the materials are necessarily not continuous within the laminate structure, and where such is the case, they are positioned precisely, one with respect to another, in the relationship they will occupy in the final products. The cover layer material and the barrier layer material are then bonded together by applying pressure in the appropriate positions, and what will become the peripheral seal is created. The seal may also be made by means of heat-bonding, ultrasonic bonding, radio frequency sealing, mechanical crimping, and the like and combinations thereof. The sealed structure is then severed by conventional means (i.e. die-cutting, fluid-jet cutting, or by laser) from the web to create a discrete article.

The preferential bending zones are created preferably by embossing. The choice of embossing is not critical since the same result may be obtained by other methods also such as slitting, perforating or other techniques known to those skilled in the art. If the embossing operation is chosen to create the preferential bending zones, the sanitary napkin is passed between a pair of rolls, one of the rolls including projections according to the pattern of embossing desired. The projections locally compress the material of the sanitary napkin, which can be either a combination of the cover layer and the absorbent system or the absorbent system alone, thereby compacting it. The degree of pressure applied during the embossing operation can vary depending upon the type of material embossed and the physical integrity of the material embossed, among others. It is within the reach of a person skilled in the art to find the optimal process conditions in accordance with the specific application. In general, the embossing pressure should be selected to sufficiently densify the material locally so as to create the preferential bending zones and at the same time not to be too high so as to sever the material. Heating the embossing rolls has been found beneficial. Also, ultrasonic embossing may be used for forming the preferential bending zones.

It is preferred to emboss the entire sanitary napkin as the embossing also holds the various layers of the sanitary napkin together and reduces the likelihood of the cover layer or the barrier layer gapping or coming loose when the sanitary napkin is bent.

The positioning adhesive material is then applied to the barrier layer in the appropriate positions, and release paper is applied to cover the positioning adhesive. Alternatively, the positioning adhesive, or the positioning adhesive and the release paper may be applied to the web before the individual articles are severed therefrom.

As indicated earlier, the sanitary napkin 20 has a thickness of about 5 mm or less. The apparatus required to measure the thickness of the sanitary napkin is a footed dial (thickness) gauge, available from Ames, with foot 1⅛" diameter with stand, 2 oz. deadweight accurate to 0.001". A digital type apparatus is preferred. If the sanitary napkin sample is individually folded and wrapped, the sample is unwrapped and carefully flattened by hand. The release paper is removed from the sample and it is repositioned back gently across the positioning adhesive lines so as not to compress the sample, ensuring that the release paper lies flat across the sample. Flaps (if any) are folded back under the sample, prior to taking the thickness reading in the center of the sample.

The foot of the gauge is raised and the sample is placed on the anvil such that the foot of the gauge is approximately centered to the sample (or in the location of interest on the sample of interest). When lowering the foot, care is taken to avoid allowing the foot to "drop" or that undue force is not applied. The read out is allowed to stabilize for approximately 5 seconds. The thickness reading is then taken.

The flexural resistance of the sanitary napkin is preferably in the range from about 400 g to about 800 g. The flexural resistance of a sanitary napkin is measured by peak bending stiffness. Peak bending stiffness is determined by a test that is modeled after the ASTM D 4032-82 CIRCULAR BEND PROCEDURE, the procedure being considerably modified and performed as follows. The CIRCULAR BEND PROCEDURE is a simultaneous multi-directional deformation of a material in which one face of a specimen becomes concave and the other face becomes convex. The CIRCULAR BEND PROCEDURE gives a force value related to flexural resistance, simultaneously averaging stiffness in all directions.

The apparatus necessary for the CIRCULAR BEND PROCEDURE is a modified Circular Bend Stiffness Tester, having the following parts:

1. A smooth-polished steel plate platform which is 102.0 mm by 102.0 by 6.35 mm having an 18.75 mm diameter orifice. The lap edge of the orifice should be at a 45 degree angle to a depth of 4.75 mm;
2. A plunger having an overall length of 72.2 mm, a diameter of 6.25 mm, a ball nose having a radius of 2.97 mm and a needle-point extending 0.88 mm therefrom having a 0.33 mm base diameter and a point having a radius of less than 0.5 mm, the plunger being mounted concentric with the orifice and having equal clearance on all sides. Note that the needle-point is merely to prevent lateral movement of the test specimen during testing. Therefore, if the needle-point significantly adversely affects the test specimen (for example, punctures an inflatable structure), than the needle-point should not be used. The bottom of the plunger should be set well above the top of the orifice plate. From this position, the downward stroke of the ball nose is to the exact bottom of the plate orifice;
3. A force-measurement gauge and more specifically an Instron inverted compression load cell. The load cell has a load range of from about 0.0 to about 2000.0 g;
4. An actuator and more specifically the Instron Model No. 1122 having an inverted compression load cell. The Instron 1122 is made by the Instron Engineering Corporation, Canton, Mass.

In order to perform the procedure for this test, as explained below, five representative sanitary napkins are necessary. From one of the five napkins to be tested, some number "Y" of 37.5 mm by 37.5 mm test specimens are cut. Specimens having portions in which a cover layer is joined directly to a barrier layer or which are a laminate of a cover layer, and a barrier layer without any component of the absorbent system, should not be tested. This test is more concerned with the overall flexibility of the sanitary napkin and not merely the peripheral portions thereof and, therefore, the flexibility of the present invention is more concerned with the flexibility of the absorbent portions of the sanitary napkin.

The test specimens should not be folded or bent by the test person, and the handling of specimens must be kept to a minimum and to the edges to avoid affecting flexural-resistance properties. From the four remaining sanitary napkins, an equal number "Y" of 37.5 mm by 37.5 mm specimens, identical to the specimens cut from the first napkin, are cut. Thus, the test person should have "Y" number of sets of five identical specimens.

The procedure for the CIRCULAR BEND PROCEDURE is as follows. The specimens are conditioned by leaving them in a room that is 21 degree Celsius plus or minus 0.1 degree Celsius and 50% plus or minus 2% relative humidity for a period of two hours. The test plate is leveled. The plunger speed is set at 50.0 cm per minute per full stroke length. A specimen is centered on the orifice platform below the plunger such that the cover layer 42 of the specimen is facing the plunger and the barrier layer 50 of the specimen is facing the platform. The indicator zero is checked and adjusted, if necessary. The plunger is actuated. Touching the specimen during the testing should be avoided. The maximum force reading to the nearest gram is recorded. The above steps are repeated until all five of the identical specimens have been tested.

CALCULATIONS

The peak bending stiffness for each specimen is the maximum force reading for that specimen. Remember that "Y" number of sets of five identical specimens were cut. Each set of five identical specimens is tested and the five values received for that set are averaged. Thus, the test person now has an average value for each of the "Y" sets tested. The flexural resistance for a sanitary napkin is the greatest of these average peak bending stiffnesses.

Applications of the product and methods of the present invention for sanitary and other health-care uses can be accomplished by any sanitary protection, incontinence, medical and absorbent methods and techniques as are presently or prospectively known to those skilled in the art. Thus, it is intended that the present application cover the modifications and variations of this invention provided that they come within the scope of the appended claims and their equivalents.

What is claimed is:

1. A sanitary napkin adapted to be worn in a crotch portion of an undergarment, said sanitary napkin comprising:
   a) a fluid-pervious cover layer;
   b) an absorbent system under said cover layer said absorbent system having a central width of at least 64 mm;
   c) a liquid-impervious barrier layer under said absorbent system;
   d) said sanitary napkin being characterised by a thickness less than about 5 mm;
   e) said sanitary napkin being characterised by a flexural resistance of not less than about 400 g;
   f) said sanitary napkin having a main body with a longitudinal axis and two opposite longitudinal side areas, said sanitary napkin including a preferential bending line extending obliquely in relation to said longitudinal axis on said main body, said preferential bending line extending from one longitudinal side area of the sanitary napkin to an opposite longitudinal side area, crossing the longitudinal axis of the sanitary napkin.

2. A sanitary napkin as defined in claim 1, wherein said bending line is formed by embossing said absorbent system.

3. A sanitary napkin as defined in claim 2, wherein said sanitary napkin includes a plurality of preferential bending lines crossing one another and defining an array of crossing points thereby forming at least one preferential bending zone allowing said sanitary napkin to fold at said preferential bending zone in response to lateral compression applied to said napkin and permitting said napkin to acquire a three-dimensional deformation profile.

4. A sanitary napkin as defined in claim 3, wherein the crossing points in the array of crossing points extend along the longitudinal axis and facilitate folding of said sanitary napkin at a location along the longitudinal axis.

5. A sanitary napkin as defined in claim 4, wherein said preferential bending zone is a central preferential bending zone, said absorbent system further including a pair of linear preferential bending zones extending between said central preferential bending zone and respective side edges of said sanitary napkin.

6. A sanitary napkin as defined in claim 1, wherein said three dimensional deformation profile is a W profile.

7. A sanitary napkin as defined in claim 1, wherein said three dimensional deformation profile is a M profile.

8. A sanitary napkin as defined in claim 1, wherein said sanitary napkin includes a pair of longitudinally extending side edges, said absorbent system comprises a top surface and a bottom surface and includes:
   two preferential bending zones extending along said longitudinal axis and being adjacent the side edges of said napkin on said top surface of said absorbent system; and
   a preferential bending zone on the bottom surface of said absorbent system extending along said longitudinal axis, between the two preferential bending zones adjacent the side edges of said napkin.

9. A sanitary napkin as defined in claim 1, wherein said sanitary napkin includes a pair of longitudinally extending side edges, said absorbent system comprises a top surface and a bottom surface and includes:
   two preferential bending zones extending along said longitudinal axis and being adjacent the side edges of said napkin on said bottom surface of said absorbent system; and
   a preferential bending zone on the top surface of said absorbent system extending along said longitudinal axis, between the two preferential bending zones adjacent the side edges of said napkin.

10. A sanitary napkin as defined in claim 6, wherein one of said preferential bending zones extending is formed by a process selected from the group consisting of perforating, slitting, cutting and embossing.

11. A sanitary napkin as defined in claim 6, wherein the two preferential bending zones extending longitudinally near the side edges of said napkin are arcuate.

12. A sanitary napkin as defined in claim 6, wherein said preferential bending zone extending longitudinally in the central portion of said napkin is comprised of a continuous line of embossing.

13. A sanitary napkin as defined in claim 6, comprising an elongated strip of material adjacent one of the top surface or bottom surface of said absorbent system and extending along said longitudinal axis, said elongated strip of material inducing said absorbent system to fold about the preferential bending zone between the two preferential bending zones adjacent the side edges of said napkin, in a direction away from said strip.

14. A sanitary napkin as defined in claim 1, wherein said absorbent system includes superabsorbent material.

15. A sanitary napkin as defined in claim 12, wherein said absorbent system includes a blend of cellulosic fibers and superabsorbent material.

16. A sanitary napkin as defined in claim 13, wherein said absorbent system includes an absorbent layer having a basis weight of from about 100 g/m2 to about 700 g/m2 which has been air-laid as a bottom stratum of pulp, a middle stratum of pulp and superabsorbent polymer disposed in amongst the pulp, and a top stratum containing at least some pulp.

17. A sanitary napkin as defined in claim 14, wherein said absorbent system includes a plurality of absorbent layers in a superposed condition.

18. A sanitary napkin as defined in claim 1, wherein said sanitary napkin includes a fastener for retaining said sanitary napkin on an undergarment of a wearer.

19. A sanitary napkin as defined in claim 16, wherein said fastener includes a flap.

* * * * *